United States Patent [19]

Hill et al.

[11] Patent Number: 4,655,885
[45] Date of Patent: Apr. 7, 1987

[54] SURFACE-MODIFIED ELECTRODE AND ITS USE IN A BIOELECTROCHEMICAL PROCESS

[75] Inventors: Hugh A. O. Hill, Cumnor Hill; David J. Page, Margate; Nicholas J. Walton, New Hinksey; David Whitford, Kidlington, all of England

[73] Assignee: National Research Development Corporation, London, United Kingdom

[21] Appl. No.: 817,570

[22] Filed: Jan. 10, 1986

[30] Foreign Application Priority Data

Jan. 11, 1985 [GB] United Kingdom ................ 8500729

[51] Int. Cl.$^4$ ........................ C25B 3/02; C25B 11/06; H01M 4/96
[52] U.S. Cl. ................................. 204/72; 204/290 R; 204/294; 429/43; 429/213; 502/101
[58] Field of Search .................... 204/290 R, 294, 72; 429/27, 42, 43, 212, 213, 215; 502/101

[56] References Cited

U.S. PATENT DOCUMENTS

| | | | |
|---|---|---|---|
| 4,318,784 | 3/1982 | Higgins et al. | 204/73 R |
| 4,414,080 | 11/1983 | Williams et al. | 204/290 R |
| 4,439,302 | 3/1984 | Wrighton et al. | 204/290 R |
| 4,461,691 | 7/1984 | Frank | 204/290 R |
| 4,490,464 | 12/1984 | Gorton et al. | 204/290 R |
| 4,510,214 | 4/1985 | Crouse et al. | 204/294 |
| 4,541,908 | 9/1985 | Niki et al. | 204/290 R |
| 4,581,336 | 4/1986 | Malloy et al. | 204/403 |
| 4,595,479 | 6/1986 | Kimura et al. | 204/294 |

FOREIGN PATENT DOCUMENTS

| | | | |
|---|---|---|---|
| 0089264 | 6/1982 | Japan | 204/290 R |
| 0060818 | 4/1984 | Japan | 204/294 |
| 2105750B | 3/1983 | United Kingdom . | |

OTHER PUBLICATIONS

I. Taniguchi et al., J. Chem. Soc., Chem. Commun., 1032 (1982).
M. J. Eddowes and H. A. O. Hill, Faraday Discuss. Chem. Soc., 331-341 (1982).
P. M. Allen et al., J. Electroanal. Chem., 178, 69-86 (1984).
F. A. Armstrong et al., J. Amer. Chem. Soc., 106, 921-923 (1984).
H. A. O. Hill et al., J. Electroanal. Chem., 87, 315-324 (1985).

Primary Examiner—Terryence Chapman
Attorney, Agent, or Firm—Murray and Whisenhunt

[57] ABSTRACT

In a bioelectrochemical process in which the electrons are transferred directly, without use of a mediator, such as a redox dye or cofactor, between an electrode and an electroactive biological material, such as an enzyme or a protein, in either direction, rapid electron transfer has previously been achieved between an electrode and the positively charged protein horse-heart cytochrome c by adding a surface-modifier such as 4,4'-bipyridyl or a derivative thereof.

It has now been found possible to promote electron transfer to either a positively or a negatively charged protein using the same surface-modifier for either job, namely a compound of formula

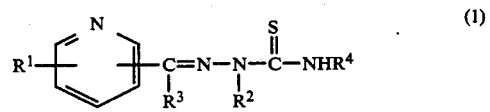

(1)

wherein:
the pyridine ring shown is substituted in the 2-, 3- or 4-position by the (methylene)hydrazinecarbothioamide group shown;

$R^1$ represents hydrogen atom(s) or one or two methyl or ethyl groups in the 2-,3- or 4-position (when the said position is not substituted by the (methylene)hydrazinecarbothioamide group shown);
$R^2$ represents a hydrogen atom or a methyl group;
$R^3$ represents a hydrogen atom or a methyl group; and
$R^4$ represents a hydrogen atom or a methyl group.

7 Claims, 4 Drawing Figures

SURFACE-MODIFIED ELECTRODE AND ITS USE IN A BIOELECTROCHEMICAL PROCESS

BACKGROUND OF THE INVENTION

1. Field of the Invention

This invention relates to a surface-modified electrode and its use in a bioelectrochemical process in which electrons are transferred directly between an electrode and an electroactive biological material which is capable of accepting or donating one or more electrons. Many such materials are redox species having a reduced state in which they can accept electron(s) and an oxidised state in which they can donate electron(s). Bioelectrochemical processes of the above kind include processes of carrying out enzymatic reactions, especially for oxidising or reducing organic compounds, in which electrons are transferred from the electrode to the enzyme, to a protein with which an enzyme is complexed or to a cofactor. Other bioelectrochemical processes involve using the energy of biological materials, e.g. enzyme-producing bacteria, to donate electrons to an electrode and thereby drive a fuel cell.

The invention is concerned with a process of direct electron transfer, whereby electrons are transferred directly (mediatorlessly) to the electroactive biological material without the intervention, in that transfer, of any other redox species. Typical mediators are redox dyes and cofactors such as NAD(H) and NADP(H). The bioelectrochemical processes with which the invention is concerned involve the adsorption of the electroactive material from solution onto the surface of the electrode, whereat the electron transfer takes place directly between electrode and electroactive material.

2. Description of the Prior Art

A bioelectrochemical process of the above kind was first described in UK Pat. No. 2033428B (National Research Development Corporation). The corresponding U.S. Pat. No. 4,318,784. The patent described a process in which direct electron transfer takes place from a gold electrode to a protein exemplified by a methane monooxygenase enzyme derived from *Methylosinus trichosporium*, an enzyme complex of cytochrome p450, putidaredoxin and putidaredoxin reductase, and cytochrome c. The patent recommends use of 4,4'-bipyridyl or 1,2-bis(4-pyridyl)ethene as a promotor of the electron transfer. Subsequently, I. Taniguchi et al., J. Chem. Soc., Chem. Commun. 1032 (1982) reported 4,4'-dithiopyridine, otherwise known as bis(4-pyridyl) bisulphide, as a promotor. The process is primarily of interest to supply reducing equivalents which re-convert the oxidised form of an enzyme to its reduced form, for the enzyme catalysis of organic oxidation reactions. In other words, organic chemical reactions are driven by supplying electrical energy.

The 4,4'-bipyridyl-like promotor is not a mediator, but appears to be adsorbed onto the electrode surface to provide a suitable interface for attracting the protein. The protein most extensively studied is horse-heart (HH) cytochrome c. HH cytochrome c is known to contain residues of the amino acid lysine in a ring around the heme edge of the protein and it is believed that when HH cytochrome c forms a complex with a redox enzyme, electron transfer takes place via the heme edge. The theory is that the function of the promotor is to attract the heme edge of the cytochrome c to face the electrode. The $\epsilon$-amino groups of the lysine residues near the heme edge might hydrogen-bond to the N-atom of a pyridine ring nitrogen of the 4,4'-bipyridyl molecule, the other end of which is possibly "perpendicularly" adsorbed on the electrode surface. See, for example, M. J. Eddowes and H. A. O. Hill, Faraday Discuss. Chem. Soc. 74, 331–341 (1982).

UK Pat. No. 2105750B (National Research Development Corporation) describes a bioelectrochemical process of the same kind but using a different type of electrode. Whereas in the specific description of the earlier patent gold electrode was used and the promotor was added to the electrolyte, the second patent uses an electrode incorporating a "binding species" therewithin. The binding species comprises ionic functional groups or non-ionic species giving rise to a dipole. The electroactive biological material has an oppositely charged site close to the electron transfer portion thereof, so that the biological material becomes temporarily bound to the electrode at the charged site. In the particular embodiments disclosed, the electrode is of graphite and the binding species is either an oxidised group produced by surface-oxidation of the graphite or a $C_{10}$–$C_{30}$ fatty acid incorporated in the body of the graphite electrode during manufacture. The theory is that the binding species provides $COO^-$ or similar groups which, at appropriate pH, attract positively charged $NH_3^+$ groups in the lysine residues of HH cytochrome c. The binding species is therefore similar in its theorised action to a 4,4'-bipyridyl promotor, except that it is apparently attracted to lysine residues by electrostatic rather than hydrogen bonding.

Recently, P. M. Allen et al., J. Electroanal. Chem 178, 69–86 (1984), examined 54 bifunctional organic compounds to assess their ability to promote the direct electrochemistry of horse-heart cytochrome c at a gold electrode. The assessment gave rise to the conclusion that successful promotors are of the general formula X⁓Y, where X represents a group which adsorbs or binds to the gold surface through a nitrogen, phosphorus or sulphur atom, Y represents an anionic or weakly basic functional group which binds to the positively charged cytochrome c protein ionically or by hydrogen bonding, and the wavy line joining X and Y represents a chemical linkage which can be conformationally rigid or flexible, but which must direct the binding group Y outwardly from the surface of the electrode when group X is adsorbed or bound to the electrode. These X⁓Y promotors are termed "surface modifiers" by P. M. Allen et al., and the same terminology will be used hereinafter. Examples of these surface modifiers are 4-mercaptopyridine, 4-mercaptoaniline, 2,3-dimercaptosuccinic acid, thiodiethanoic acid, 3,3'-thiobis(-propanoic acid), 2,2'-thiobis(succinic acid), 4,4'dithiopyridine, dithiobis(ethanoic acid), 2,2'-dithiobis(succinic acid), 3-thiophenethanoic acid acid, sodium monothiophosphate, 1,2-bis(4-pyridyl)ethene, 2,5-bis(4-pyridyl)-1,3,4-thiadiazole, pyridine-4-sulphonic acid and 4-pyridylphosphonic acid. Some of these compounds required pre-activation of the surface of the electrode with 4,4,'-dithiopyridine, followed by polishing the electrode.

Negatively-charged proteins such as rubredoxin and 2[4Fe-4S] ferredoxin do not give electron transfer with a graphite electrode as described above. However, when a multivalent cation such as $Mg^{2+}$ is added, they do give electron transfer, F. A. Armstrong et al., J. Amer. Chem. Soc. 106, 921–923 (1984). Clearly, the divalent $Mg^{2+}$ cation bridges between the negatively charged species in the electrode and the negatively charged site in the protein.

SUMMARY OF THE INVENTION

It has now been found that certain organic compounds will promote direct electron transfer between an electrode and a negatively charged protein and still further research has produced a class of compounds which, amazingly, are surface modifiers for both positively and negatively charged proteins.

It has now been found that compounds of formula

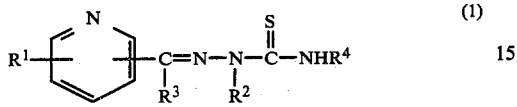

wherein:

the pyridine ring shown is substituted in the 2-, 3-or 4-position by the (methylene)hydrazinecarbothioamide (MHC) group shown;

$R^1$ represents hydrogen atom(s) or one or two methyl or ethyl groups in the 2-,3- or 4-position (when the said position is not substituted by the (methylene)hydrazinecarbothioamide group shown);

$R^2$ represents a hydrogen atom or a methyl group;

$R^3$ represents a hydrogen atom or a methyl group; and $R^4$ represents a hydrogen atom or a methyl group.

The compounds of formula (1) having these surface-modifying properties are (pyridinylmethylene)hydrazinecarbothioamides, hereinafter termed "PMHCs", and simple substitution derivatives thereof.

The invention includes electrodes, especially of gold, having a surface modified with a compound of formula (1). It further includes a process of preparing such a modified electrode which comprises adsorbing the compound of formula (1) onto the electrode surface. The use of the surface modifiers in the promotion of electron transfer is within the invention and also covered is a bioelectrochemical process of the kind described above. Such a bioelectrochemical process can be in either direction. Thus it includes a process in which electrons are supplied to an enzyme or to a protein which complexes with an enzyme thereby to drive a reaction, especially an organic reaction, catalysed by the enzyme. In the reverse direction, it covers a fuel cell in which energy from an organic reaction or a biological transformation is harnessed to produce electricity and possibly a useful by-product from the reaction or transformation.

According to a feature of the invention there is provided a bioelectrochemical process in which electrons are transferred directly between an electrode and an electroactive biological material which is not permanently bound to the electrode, said electroactive biological material having an electron transfer portion capable of receiving and donating electrons and also having close thereto a charged region, characterised in that a surface-modified electrode of the invention is used in the process.

DESCRIPTION OF THE PREFERRED EMBODIMENTS

The preferred compounds of formula (1) are the PMHCs themselves, these being the compounds in which $R^1$, $R^2$, $R^3$ and $R^4$ are all hydrogen atoms, i.e. of formula

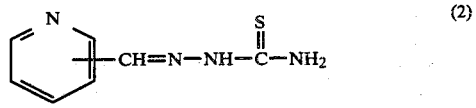

wherein the MHC group shown is a 2-, 3- or 4-position substituent of the pyridine ring.

The corresponding (benzenylmethylene)hydrazinecarbothioamides "BHMCs" do not serve as promotor for negatively or positively charged proteins. It is speculated that the PMHC derivatives are adsorbed on the electrode with the plane of the pyridine ring perpendicular to the plane of the electrode surface, whereas the BMHCs appear to be oriented so that the plane of the benzene ring lies "flat" or approximately parallel to the plane of the electrode surface.

The PMHCs, which are known compounds, and their derivatives can be prepared from the aldehyde or ketone and the appropriately substituted or unsubstituted thiosemicarbazide, according to the reaction scheme

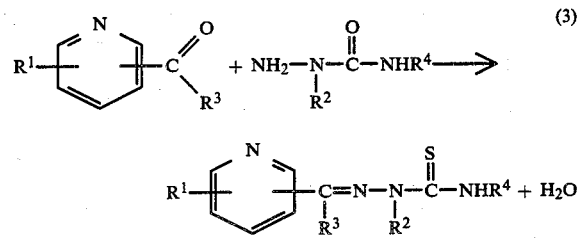

where $R^1$, $R^2$, $R^3$ and $R^4$ and the pyridine ring substitution are as defined above.

P. M. Allen et al., supra, found that in many instances the selectivity of the bonding to the electrode was improved if the electrode was "pre-activated" by polishing it with 4,4'-bipyridyl or 4,4'-dithiopyridine. The polishing appears to block some of the available sites which in some way assists the surface modifier applied subsequently to bind to the surface of the electrode in a way which presents the Y group in a favourable orientation. Such pre-activation is not necessary when using PMHCs, but with some surface modifiers could be helpful in the context of the present invention.

Figure 1A:
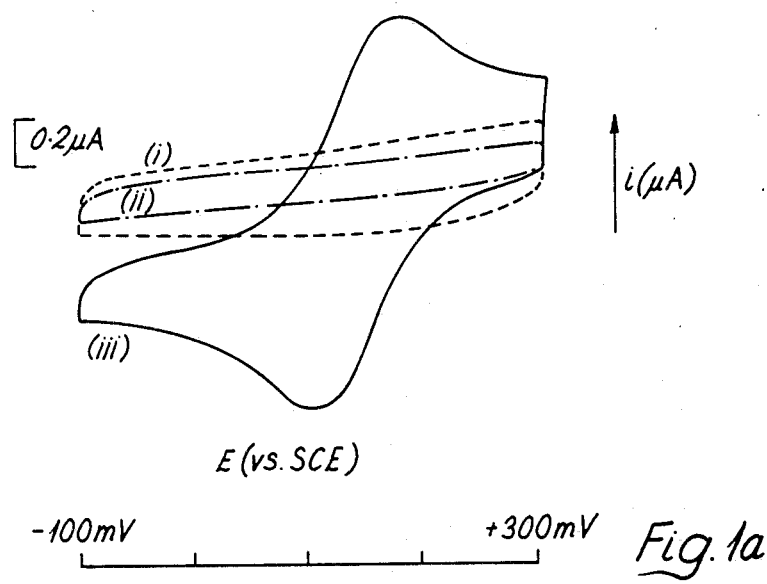
FIG. 1 shows d.c. cyclic voltammograms (a) and (b) of electric potential versus current using various test electrodes (i)–(vi) having a modified or unmodified surface and using a negatively charged protein.
Figure 1B:
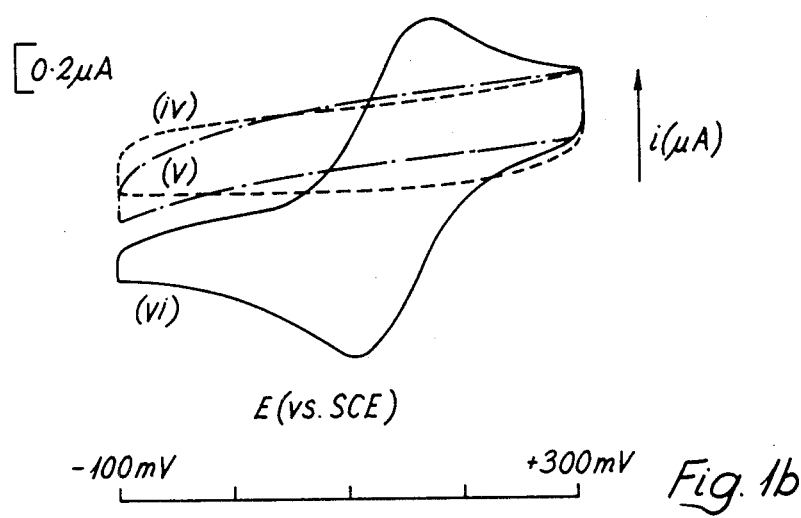
Figure 2A:
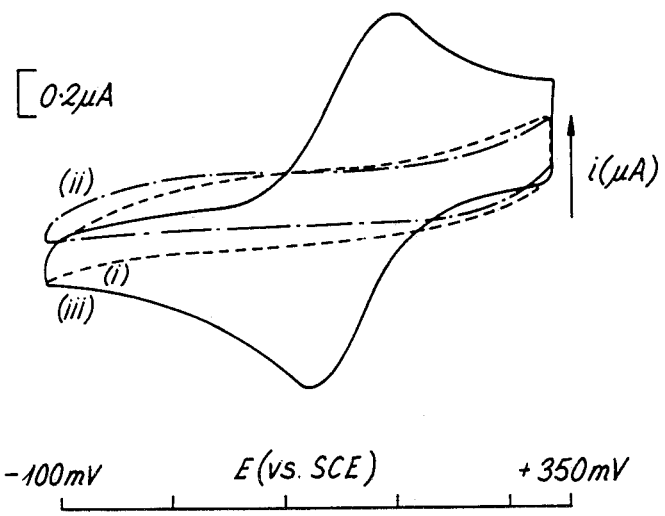
FIG. 2 shows d.c. cyclic voltammograms (a) and (b) of electric potential versus current using the same test electrodes (i)–(vi) and another negatively charged protein.
Figure 2B:
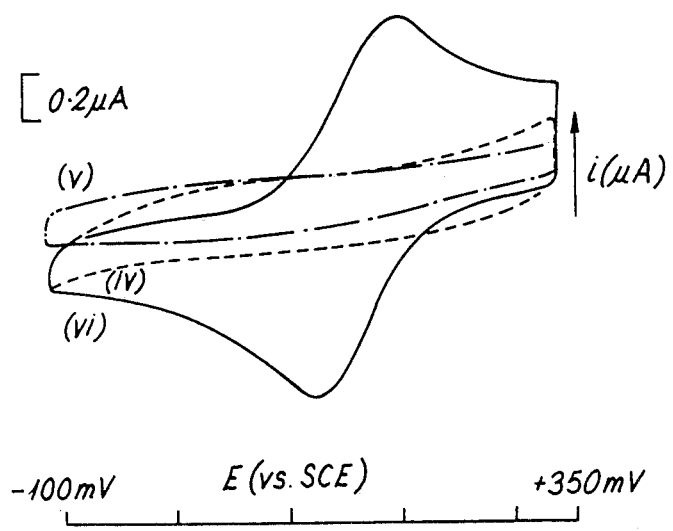

The best test known to the inventors of whether the surface modifiers really do work is to use cyclic voltammetry. A complete cycle of current produced over a range of positive and negative electrode potentials with well defined and separated peaks is characteristically produced in the voltammogram. FIGS. 1 and 2 show such voltammograms and are discussed in the Examples. Well-defined peaks denote "faradaic current", i.e. that the number of electrons being taken from the external circuit is equal to the number transferred from the electrode to the protein in solution and vice versa when the direction of electron transfer is reversed.

The invention is applicable to any positively charged electroactive biological material (EABM), e.g. mammalian cytochrome c or any of the enzymes described in the prior patents referred to. It is also applicable to any negatively charged EABM such as plasto-cyanin, multi-modified cytochrome c, rubredoxin or 2[4Fe-4S] ferredoxin as well as to EABMs approximately neutral in charge, e.g. azurin from Pseudomonas spp. Horse-heart cytochrome c has a Positive charge of 9, cytochrome $c_{551}$ (from *Pseudomonas aeruginosa*) has a negative charge of $-1$ and cytochrome $c_5$ is intermediate in its charge, which is believed to be in the region of $+4$ to 5. All these proteins are usable in the present invention. The EABM can be a protein which forms a redox couple with an enzyme, an enzyme or a cofactor. It need only possess an electron transfer portion to accept and donate electrons from and to the electrode and a charged site in sufficiently close proximity to the electron transfer portion that attraction of the charged site to face the electrode causes the electron transfer portion to become oriented into a favourable configuration with respect to the electrode for the electron transfer to take place. Put more simply, the relative disposition of the electron transfer portion and charged site of the EABM should be effectively similar to that of the lysine group and heme edge in cytochrome c.

Referring to formula (1), the MHC group (whether unsubstituted or methyl-substituted) is preferably in the 3- or 4-position of the pyridine ring. Whereas PMHCs of all three pyridine ring isomers exhibit similar electron transfer characteristics in relation to the EABMs azurin, cytochrome $c_{551}$ and cytochrome $c_5$, the 2-isomer is markedly inferior to the others when simultaneously HH cytochrome c is used as the EABM and the working electrolyte does not contain anions, such as perchlorate, which prevent formation of hydrogen bonds. It is believed that if the 2-isomer forms a hydrogen bond, as shown in formula (4):

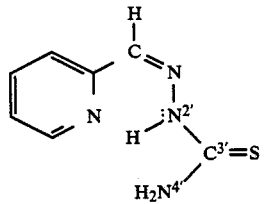
(4)

the pyridine nitrogen atom lone pair is not free to interact with the cytochrome c, thereby leading to reduce electron transfer properties. If the 2'-position is blocked by a methyl group, i.e. $R^2$ in formula (1) is $CH_3$, however, hydrogen bonding is somewhat disrupted and the performance of the surface modifier is better than that of the corresponding PMHC in which $R^2$ in formula (1) is hydrogen. When hydrogen bond formation is disrupted by anions the performance of the ring-position isomers tends to become about the same.

The electrode can be of any material compatible with the surface modifier being adsorbed or bound thereon, e.g. of a noble metal such as Pt, Pd, Ag or Au, or of graphite.

The preferred material for the electrodes is gold and it is preferred that the surface of the electrode is cleaned by polishing (to remove any oxide layer on the gold surface) before the electrode is contacted with the surface modifier. An alusmina/water slurry can be used for this purpose.

The surface modifier can be adsorbed onto the electrode in any convenient way, of which simple dipping is preferred. Since only a surface layer of the modifier is required, the requisite extent of adsorption can be produced by dipping the electrode in a solution of low concentration thereof, for example at least 0.007, preferably at least 0.01, more preferably at least 1 millimolar. Any higher concentration up to saturation of the dipping solution could of course be used. The invention is therefore extremely economical in permitting such small concentrations of the surface modifier to be used.

The following Examples illustrate the invention. They show reversible electron transfer between gold or graphite electrodes and a selection of positively charged, overall neutral and negatively charged proteins. The surface modifiers used are 2-PMHC, 3-PMHC, 4-PMHC and derivatives thereof in accordance with the invention, (benzenylmethylene)hydrazinecarbothioamide, hereinafter "BMHC", of formula:

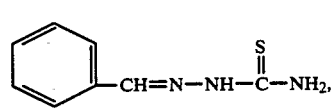
(5)

and 2-aminoethanethiol, hereinafter "AET" ($HS-CH_2CH_2-NH_2$), dithiobisethanamine, hereinafter "DTBE" ($NH_2-CH_2CH_2-S-S-CH_2-CH_2-NH_2$) and 4,4'-dithiopyridine otherwise termed bis(4-pyridyl)bisulphide, hereinafter "DPBS", of formula:

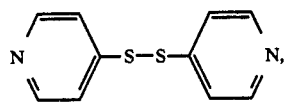
(6)

all for comparative purposes.

EXAMPLES

Materials and methods

Direct current (d.c.) cyclic voltammograms were obtained using an Oxford Electrodes Ltd. potentiostat and recorded on a Bryans 26000 X-Y recorder. First and third cycle and steady state voltammograms were recorded. A 4 mm diameter gold disc working electrode (except in Example 5 where a graphite electrode was used), platinum gauze counter electrode and saturated calomel reference electrode (Radiometer K401) were used in a glass cell having a working compartment approximately 500 μl in volume. Except where otherwise stated the working compartment was filled with a solution of the protein (165 μM), sodium dihydrogen phosphate buffer (20 mM) sodium perchlorate (100 mM) and adjusted to the stated pH, usually 7 or 7.5, with sodium hydroxide. The sodium perchlorate was included to increase the ionic strength of the solution. Before each experiment the working electrode was polished with a 0.3 μm alumina/water slurry on cotton wool and then washed thoroughly with Milli-Q (doubly deionised) water.

Except where otherwise stated, surface modification was performed by dipping the freshly polished gold working electrode for 2 minutes into a 1 mM solution of the surface modifier in the same buffer-perchlorate solution used in the working compartment followed by copious washing with Milli-Q water.

A sweep rate of 20 mV sec$^{-1}$ was used except where otherwise stated. The potential range used was between +400 mV and −200 mV (vs. SCE) this range being reduced according to the nature of the protein, to the minimum required to produce a cyclic voltammogram. Thus the starting and switching potentials were adjusted to ensure that they caused no distortion of the shape of the cyclic voltammograms: they were normally more than 120/n mV beyond the potentials of the peak anodic and cathodic faradaic currents, n being the number of electrons per molecule oxidised or reduced. For example, for plastocyanin the sweep was over the range +300 mV to −100 mV (vs. SCE) whilst for multi-substituted cytochrome c a range from +350 mV to −100 mV was employed.

3-PMHC was obtained from Lancaster Synthesis Ltd., as was AET, which was obtained as the hydrochloride. DTBE was obtained from the Aldrich Chemical Co. Ltd. as the dihydrochloride salt. BPBS was supplied as Aldrithiol-4, from Aldrich Chemical Co. Ltd., 2-PMHC, 4-PMHC and BMHC were synthesised from their parent aldehydes and thiosemicarbazide using standard methods, see J. Berstein et al., J. Amer. Chem. Soc. 73, 906 (1951). The properties of each compound were in good agreement with those reported, see F. E. Anderson et al., J. Amer. Chem. Soc. 73, 4967 (1951).

All the substituted PMHCs were synthesised from their parent aldehydes and substituted thiosemicarbazides using the same methods as for the unsubstituted PMHCs. The properties of each of the substituted PMHCs were in good agreement with those reported in the literature.

Spinach plastocyanin was isolated according to the method of Borchert et al., Biochem. Biophys. Acta 197, 78 (1970). The oxidised de-salted, product, having a purity ratio ($A_{275}/A_{598}$) of 1.33 or better, was stored in liquid nitrogen in pellet form.

A modified cytochrome c bearing a net negative charge was obtained using the procedure of D. L. Brautigan et al., J. Biol. Chem. 253, 130 (1978). The method involves the modification of lysines by 4-chloro-3,5-dinitrobenzoic acid (CDNB) and yields mono-, di- and multi-substituted carboxydinitrophenyl (CDNP) derivatives of cytochrome c. The multi-substituted fraction was that eluted first from a 5×100 cm CM-32 chromatography column (Whatman Biochemicals Ltd., UK) with 25 mM phosphate buffer at pH 7.8. The multi-substituted fractions (approximately 3 liters) were pooled, adjusted to 0.01 M and applied to a 1×12 cm DE52 column (Whatman Biochemicals Ltd., UK) pre-equilibrated with 50 mM sodium cacodylate-HCl, pH 7.0. Cytochrome c with a net negative charge remained bound at the top of the column whilst a small amount of less extensively modified cytochrome c was not retained by the column and eluted in the void volume. The negatively charged cytochrome c was eluted with 50 mM cacodylate-HCl PH 7.0, 0.5 M NaCl and diafiltered, using an Amicon Ultrafiltration cell with a YM10 membrane, against distilled water. The modified cytochrome was subsequently frozen in liquid nitrogen in concentrated pellet form.

Native cytochrome c was horse-heart Type VI obtained from the Sigma Chemical Co. and was chromatographed on CM-32 to remove de-amidated forms according to the method of D. L. Brautigan et al., in "Methods in Enzymology" 53, Ed. D. Fleicher and L. Packer, Academic Press, New York, pages 128–164.

Cytochrome $c_{551}$ was isolated by the method of R. P. Ambler et al., Biochem. J. 131, 485 (1973).

Cytochrome $c_5$ was isolated by the method of D. C. Carter et al., J. Mol. Biol. 184, 279 (1985).

Azurin was isolated by the method of S. R. Parr et al., Biochem. J. 157, 423–434 (1976).

All other compounds used were of AnalaR grade. All solutions were made up with Milli-Q water and degassed with oxygen-free argon before use. Experiments were undertaken at 25° C. except where otherwise stated.

EXAMPLE 1

The third cycle d.c. cyclic voltammograms were produced for spinach plastocyanin (250 μM) at pH 7.5 and sweep rate of 20 mV sec$^{-1}$, using (i) bare gold, (ii) BMHC-modified gold, (iii) PMHC-modified gold, each of the three isomers of PMHC being tested in turn, (iv) bare gold, (v) BPBS-modified gold and (vi) AET-modified gold electrodes. The third cycle voltammograms are shown in FIG. 1 of the drawings.

At bare gold electrodes, FIG. 1(i) and (iv), no faradaic currents were observed. The change in the capacitative charging current due to surface modification (in the absence of the protein) is consistent with the chemisorption of the surface modifiers to the electrode surface and consequent alteration of the interfacial capacitance. BMHC-modified gold (ii) and BPBS-modified gold (v) also showed no faradaic responses. However, in the presence of isomers of PMHC, each of which gave the said voltammogram (iii), and 2-aminoethanethiol-modified gold electrodes (vi), faradaic currents were observed. The electrochemistry of plastocyanin is well-behaved at these surface-modified electrodes (iii) and (vi).

Table 1, which follows Example 3, gives electrochemical data for Examples 1–3. The separation of the CV peak potentials ($\Delta E_{pp}$) is about 70 mV, consistent with a quasi-reversible one-electron system. It should be noted that, over the range of potentials used to study protein electrochemistry, no faradaic processes are attributable to the surface modifiers; they are thus not acting as redox mediators of electron transfer. The half-wave potential, $E_{\frac{1}{2}}$, of plastocyanin (which is independent of modifier) does not differ significantly from previously reported values. Plots of peak current ($i_p$) versus the square root of the sweep rate ($v^{\frac{1}{2}}$) are linear up to scan rates of 0.1 V sec$^{-1}$. Such plots allowed an estimation of the diffusion coefficient (D) and the heterogeneous rate constant ($k_s$) to be made. These data are given in Table 2, which follows Example 3.

The electrochemistry of plastocyanin at 25° C. is somewhat impersistent, manifest as a decrease in peak currents and an increase in peak separation. At 3° C., the electrochemistry was much more persistent. Addition of surface modifier to the bulk solution also increased the persistence.

Electron transfer between plastocyanin and the PS1 photosystem of plants is known to be sensitive to pH. Changing the pH had a dramatic effect on the electrochemistry of plastocyanin at an AET-modified electrode. At pH 8, the cyclic voltammograms corresponded to those of quasi-reversible electron transfer between the plastocyanin and the electrode. Decreasing the pH led to lower peak currents and an increase in the peak separations. At pH 6.0 and below no faradaic current was detected. It was also observed that the capacitative charging current of the AET-modified electrode (in the absence of protein) is pH-dependent. However, at PMHC-modified gold electrodes quasi-reversible electrochemistry was observed over the whole pH range, 4.5–8.0. (Thin layer electrophoresis confirmed that the PMHCs are electrostatically neutral between pH 4 and 9.)

EXAMPLE 2

Third cycle d.c. cyclic voltammograms were produced for multi-substituted CDNP-cytochrome c (165 μM) at pH 7.0, except for AET (pH 8.0), using the same electrodes as in Example 1. The steady state voltammograms are shown in FIG. 2.

Bare gold (i) and (iv) showed no faradaic current. All the isomers of PMHC (iii) showed quasi-reversible electrochemistry, but with BMHC (ii) there was no faradaic current. The BPBS-modified electrode (v) showed a small reduction faradaic current on the first cycle only. However, the AET-modified electrodes (vi) showed good faradaic responses and the separation of peak potentials of about 70 mV was consistent with quasi-reversible electron transfer.

EXAMPLE 3

D.c. cyclic voltammograms (not shown) were produced for native horse-heart cytochrome c at pH 7.5 or 8 and otherwise under the same conditions and using the same electrodes as in Example 2.

With native cytochrome c, BPBS and all the isomers of PMHC give quasi-reversible protein electrochemistry. At AET- and DTBE-modified gold electrodes, small reduction and re-oxidation currents were seen but no peaks were observed. Native cytochrome c also showed no faradaic responses at bare gold or a BMHC-modified gold electrode.

The following Tables give electrochemical data relating to Examples 1 to 3. The conditions were the same as in those Examples except that for Table 1 pHs of 7.0 to 8.0 were used and in Table 2 the pH of 7.5 was used. (The precise pH within the 7.0 to 8.0 range does not appear to influence the electrochemistry markedly, except in the case of AET, mentioned in Example 1.) At the temperature of 25° C. the electrochemistry of plastocyanin did not persist but that of the other proteins did.

TABLE 1

Electrochemical data from cyclic voltammograms of plastocyanin, native HH cytochrome c and multi-cytochrome c at gold electrodes, unmodified and surface-modified as described in Examples 1-3.

| Surface Modifier | Native HH cytochrome c $\Delta E_{pp}$ (mV) | Native HH cytochrome c $E_{\frac{1}{2}}$ (mV) | Multi-substituted CDNP-cytochrome c $\Delta E_{pp}$ (mV) | Multi-substituted CDNP-cytochrome c $E_{\frac{1}{2}}$ (mV) | Plastocyanin $\Delta E_{pp}$ (mV) | Plastocyanin $E_{\frac{1}{2}}$ (mV) |
|---|---|---|---|---|---|---|
| Bare gold | (a) | | (a) | | (a) | |
| 2-PMHC | 92 | +30 | 65 | +165 | 70 | +135 |
| 3-PMHC | 74 | +30 | — | — | 72 | +131 |
| 4-PMHC | — | — | — | — | 94 | +130 |
| AET | (b) | | 68 | +164 | 92 | +135 |
| DTBE | (b) | | 62 | +162 | 100 | +135 |
| BPBS | 68 | +30 | (c) | | (a) | |

Footnotes:
(a) No protein electrochemistry was observed.
(b) Small reduction and re-oxidation currents, no peaks observed.
(c) Small reduction current on first cycle only.

TABLE 2

Redox potential, diffusion coefficient and standard heterogeneous rate constant for plastocyanin, multi-substituted CDNP-cytochrome c as determined at pH 7.5, 25° C., by cyclic voltammetry at a gold electrode, surface-modified by 2-PMHC.

| Protein | $E_{\frac{1}{2}}$(mV vs. SCE) | D(cm$^2$ sec$^{-1}$) | $k_s$(cm sec$^{-1}$) |
|---|---|---|---|
| Spinach plastocyanin | +135 | 7.5 × 10$^{-7}$ | 4 × 10$^{-3}$ |
| Multi-substituted (CDNP) horse-heart cytochrome c | +165 | 7.9 × 10$^{-7}$ | 5 × 10$^{-3}$ |
| Native horse-heart cytochrome c | +30 | 5.0 × 10$^{-7}$ | 3 × 10$^{-3}$ |

The above Examples demonstrate that only the PMHCs promote good electrochemistry (electron transfer) of the strongly positively charged protein HH cytochrome c and the two negatively charged proteins, the plastocyanin and the multi-modified cytochrome c.

EXAMPLE 4

This Example shows the effect of varying the amount of surface modifier adsorbed on the electrode. The surface modifier used was 3-PMHC and the protein native HH cytochrome c at a concentration of 175 μM. Scan rate was 100 mV sec$^{-1}$.

The relative amount of surface modifier deposited can be expressed in terms of the length of time for which the electrode is dipped in a solution of the surface modifier (provided, of course, that the saturation amount is not reached).

Table 3 below shows the results. It is concluded that 0.0075 mM or 7.5 μM is about lowest reasonable concentration of surface modifier. While one can use less, it is likely to require an unacceptably long dipping time. The larger the value of $\Delta E_{pp}$ in Table 3, the less satisfactory the result (the voltammogram is "flatter" indicating that the maximum current in each direction was obtained at potentials which are more widely separated, representing slower electron transfer from electrode to protein and vice versa).

TABLE 3

| Concentration of 3-PMHC (mM) | Dip time (sec) | Peak to peak separation $\Delta E_{pp}$ (mV) |
|---|---|---|
| 0.75 | 15 | 75 |
| 0.75 | 5 | 75 |
| 0.075 | 5 | 130 |
| 0.075 | 30 | 100 |
| 0.075 | 120 | 90 |
| 0.0075 | 5 | 160 |
| 0.0075 | 120 | 120 |
| 0.0075 | About 1200 | 120 |

EXAMPLE 5

A polished graphite electrode in which the base plane (plane of the graphite rings) is parallel to the electrode surface was used. The graphite was obtained from Le Carbone GB Ltd. This electrode, unmodified, gave a cyclic voltammogram with HH cytochrome c, probably because there are defects in the surface in which oxidised carbon groups lie (as in UK Pat. No. 2105750B referred to above). Using 200 μM (1.6 mg/400 μl) native HH cytochrome c, the peak separation was 100 mV. When the graphite electrode was surface-modified by dipping in 4-PMHC, the peak separation was reduced to 85 mV, thus demonstrating an improvement.

EXAMPLE 6

This Example illustrates the use of cytochrome $c_5$, azurin and cytochrome $c_{551}$. The protein solution was buffered to pH 7.0 in 0.2 M sodium dihydrogen phosphate (without perchlorate). The electrode was dipped in 1 mM 4-PMHC in 0.1 M sodium dihydrogen phosphate (without perchlorate), pH 7.0. Good cyclic voltammograms were obtained. Table 4 shows the half wave potential and peak to peak separations. The results for azurin were the same irrespective of its Pseudomonas origin, i.e. whether from the species *putida, aeruginosa* or *alcaligenes*.

TABLE 4

| Protein | Half wave potential $E_{\frac{1}{2}}$(mV vs. SCE) | Peak to peak separation $\Delta E_{pp}$ (mV) |
|---|---|---|
| Cytochrome $c_5$ | +92 | 83 |
| Azurin | +70 | 75 |
| Cytochrome $c_{551}$ | +50 | 73 |

EXAMPLE 7

This Example illustrates the use of 9 different surface modifiers according to the invention with 3 different proteins. The dipping solution containing the 1 mM concentration of surface modifier was of 0.1 M sodium dihydrogen phosphate (without perchlorate), adjusted with sodium hydroxide to pH 7.0. The working compartment contained the 165 μM protein solution in 0.2 M sodium cacodylate, adjusted with sodium hydroxide to pH 6.0. The peak to peak separations obtained in the cyclic voltammograms are shown in Table 5 below. It will be seen that in the absence of anions which disrupt formation of hydrogen bonds the 4-position isomers are superior to the 3-position isomers which are in turn markedly superior to the 2-position isomers when the protein is the highly positively charged HH cytochrome c. With the other, less highly positively charged, proteins, there is little difference between the ring isomers. Except in the case of the 2'-methyl group of the 2'-isomer, which appears to reduce the postulated hydrogen bonding effect, the introduction of methyl groups had little effect on the performance of the surface modifers.

TABLE 5

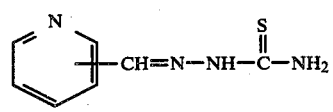

| Ring isomer | $R^2$ | $R^4$ | Native HH cytochrome c $\Delta E_{pp}$ (mV) | Cytochrome $c_{551}$ $\Delta E_{pp}$ (mV) | Azurin $\Delta E_{pp}$ (mV) |
|---|---|---|---|---|---|
| 2- | H | H | >250 | 67 | 75 |
| 2- | CH$_3$ | H | 190 | 63 | 70 |
| 2- | H | CH$_3$ | >250 | 77 | 88 |
| 3- | H | H | 130 | 65 | 75 |
| 3- | CH$_3$ | H | 115 | 70 | 83 |
| 3- | H | CH$_3$ | 115 | 68 | 77 |
| 4- | H | H | 75 | 67 | 80 |
| 4- | CH$_3$ | H | 135 | 65 | 80 |
| 4- | H | CH$_3$ | 113 | 67 | 80 |

We claim:

1. An electrode having a surface modified with a (pyridinylmethylene)hydrazinecarbothioamide, hereinafter termed "PHMC", or a derivative thereof of formula

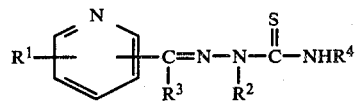

wherein:
the pyridine ring shown is substituted in the 2-, 3- or 4-position by the (methylene)hydrazinecarbothioamide group shown;
$R^1$ represents hydrogen atom(s) or one or two methyl or ethyl groups in the 2-,3- or 4-position (when the said position is not substituted by the (methylene)-hydrazinecarbothioamide group shown);
$R^2$ represents a hydrogen atom or a methyl group;
$R^3$ represents a hydrogen atom or a methyl group; and
$R^4$ represents a hydrogen atom or a methyl group.

2. An electrode having a surface modified with a PMHC of formula (2)

(structure: pyridine ring—CH=N—NH—C(=S)—NH$_2$)

wherein the pyridine ring substituent is in the 2-, 3- or 4-position.

3. An electrode according to claim 1, made of a noble metal.

4. An electrode according to claim 3, wherein the surface has been modified by dipping it in a solution of the modifier of concentration from 0.007 millimolar (7 micromolar) to saturation.

5. An electrode according to claim 1 made of graphite.

6. In a bioelectrochemical process which comprises supplying electric current to an electrode, positioning an electroactive biological material (EABM) in electron transfer relationship therewith but so that it is not permanently bound to the electrode, said EABM having an electron transfer portion capable of receiving and donating electrons and also having close thereto a charged region so that the EABM becomes temporarily bound to the electrode at the charged site, whereby electrons are transferred directly from the electrode to the EABM and harnessing the EABM to drive a chemical reaction, or in the reverse direction, supplying electrons produced from a chemical reaction or biological transformation to the EABM, whereby they are transferred from the EABM to the electrode and harnessed to produce electricity in a fuel cell, the improvement wherein said electrode is a surface-modified electrode defined in claim 1.

7. In a bioelectrochemical process which comprises supplying electric current to an electrode, positioning an electroactive biological material (EABM) in electron transfer relationship therewith but so that it is not permanently bound to the electrode, said EABM having an electron transfer portion capable of receiving and donating electrons and also having close thereto a charged region so that the EABM becomes temporarily bound to the electrode at the charged site, whereby electrons are transferred directly from the electrode to the EABM and harnessing the EABM to drive a chemical reaction, or in the reverse direction, supplying electrons produced from a chemical reaction or biological transformation to the EABM, whereby they are transferred from the EABM to the electrode and harnessed to produce electricity in a fuel cell, the improvement wherein said electrode is a surface-modified electrode defined in claim 2.

* * * * *